Oct. 18, 1960 H. C. SWIM Plant Pat. 1,976
PEACH TREE
Filed Jan. 4, 1960
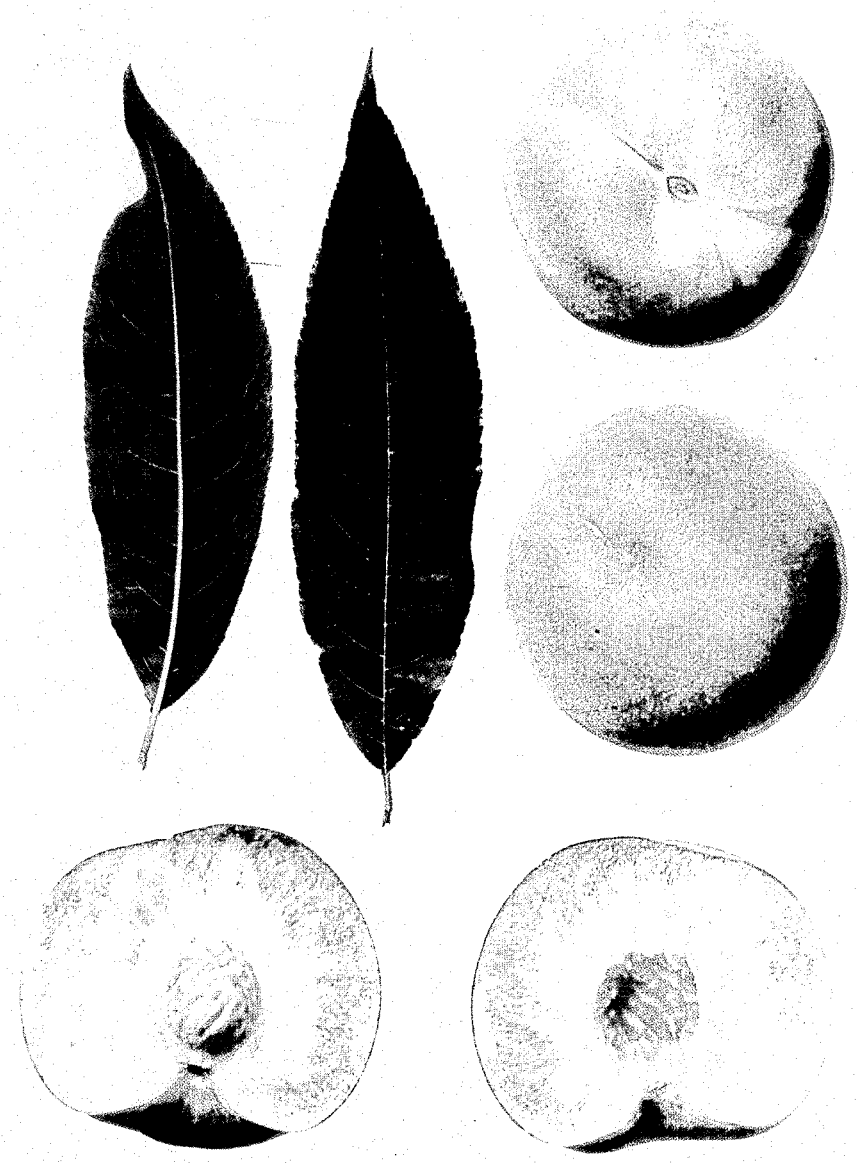
Inventor.
H. C. Swim
By: Robert Cobb
Attorneys.

United States Patent Office

Plant Pat. 1,976
Patented Oct. 18, 1960

1,976

PEACH TREE

Herbert C. Swim, Ontario, Calif., assignor to Armstrong Nurseries, Inc., Ontario, Calif., a corporation of California Filed Jan. 4, 1960, Ser. No. 456

1 Claim. (Cl. 47—62)

The present invention relates to a new and distinct variety of peach tree of the white-fleshed, freestone, fruit-bearing type, which was originated by me by crossing two unnamed and unpatented sister seedlings, each derived from a cross of an unnamed and unpatented seedling of "Chinese Dwarf" (unpatented) × "Rio Oso Gem" (Plant Patent No. 84) and an unnamed and unpatented seedling of "Babcock" (unpatented × "Mayflower" (unpatented).

The primary objective of this breeding was to produce an improved, early-ripening peach variety of either the while or yellow-fleshed type. This objective was fully achieved as a white-fleshed peach, along with other desirable features, as evidenced by the following unique combination of characteristics which distinguish the new variety from its parents, as well as from all other varieties of which I am aware:

(1) A vigorous tree, with a chilling requirement about equal to that of the variety known as "Springtime" (Plant Patent No. 1,268);

(2) Medium-sized white-fleshed freestone fruit of good subacid flavor;

(3) Fruit of almost round shape and having the apex somewhat depressed;

(4) Very attractive red coloring of the skin of the fruit; and (5) A ripening period in southern California which ranges from a few days earlier to a few days later than that of the variety known as "Robin" (Plant Patent No. 529), the variation being principally due to the difference in chilling requirement and resulting difference in the times of bloom from season-to-season.

In comparison with the "Robin" peach referred to above, my new variety has a maturation period in southern California averaging from about five days to about a week longer, with a lower chilling requirement, while the flavor of the fruit is subacid instead of very sweet like that of "Robin." In color and size of the fruit, the new variety appears to be better on the average than that of "Robin."

The improvements achieved in my new variety may be further noted and clarified by a comparison thereof with the variety known as "Redwing" (Plant Patent No. 621). In this connection, the new variety ripens from two to three weeks earlier than "Redwing," has a chilling requirement considerably lower, and the length of the maturation period of the fruit is from one to two weeks shorter than that of "Redwing."

The unnamed seed parent of my new variety was characterized by bearing white-fleshed, freestone fruit of good size, good flavor, and fair skin color, said fruit ripening in early August, while the fruit of my new variety ripens on the average from six to eight weeks earlier, and the fruit has a much better red skin color.

The pollen parent of the new variety was characterized by its white-fleshed, semi-cling fruit of relatively small size and good skin color, but of somewhat bitter flavor, with the fruit ripening in the period of mid-June, while in comparison with this parent, the fruit of my new variety is larger, more freestone, and has no bitterness in flavor.

In comparison with the antecedents of my new variety, and considering first the original ancestor "Chinese Dwarf," that ancester is characterized by its white-fleshed, cling fruit of small size, litle skin color, and soft flesh, with a ripening period in late August. The trees of "Chinese Dwarf" have a very low chilling requirement. Contrary to the dwarf nature of "Chinese Dwarf," my new variety is characterized by having a tall type of tree growth, with a somewhat higher, though still only moderate chilling requirement. The fruit of the new variety is larger, better colored, firmer, more freestone, and ripens some ten weeks earlier.

The original ancester "Rio Oso Gem" has yellow-fleshed, freestone fruit of good size, flavor, quality, and firmness, said fruit ripening in early August, whereas the fruit of my new variety is white-fleshed, smaller, and ripens some eight weeks earlier, and the tree of my new variety is more vigorous and has a lower chilling requirement.

The original ancester "Babcock" is characterized by small to medium-sized, white-fleshed, freestone fruit of good skin color and sweet flavor, with a ripening period from early to mid-July, while the fruit of my new variety is not quite as sweet in flavor, but has somewhat better size, and ripens approximately one month earlier than the fruit of this ancestor.

The original ancester "Mayflower" is characterized by its white-fleshed, cling fruit of small to medium size, moderate skin color, and soft flesh, with a ripening period in late May, and the tree has a high chilling requirement and the yield is low. In contrast thereto, the fruit of my new variety is of much better size and skin color, has firmer flesh, and ripens two or three weeks later, and the tree has a much lower chilling requirement and a much better yield.

Asexual reproduction of my new variety, as performed by grafting at Ontario, California, shows that the foregoing characteristics and distinctions come true to form and are established and transmitted through succeeding propagations.

The accompanying drawing shows typical specimens of the foliage and fruit of my new variety, with the upper and lower surfaces of the foliage being illustrated, and with both exterior and sectional views of the fruit being shown, all as depicted in color as nearly true as it is reasonably possible to make the same in a color illustration of this character.

The following is a detailed description of my new variety, as based upon observations of specimens grown at Ontario, California, with color terminology in accordance with Robert F. Wilson's Horticultural Colour Chart (hereinafter abbreviated as "Wilson") and Ridgway's Color Standards and Nomenclature (hereinafter abbreviated as "Ridgway"), except where general color terms of ordinary dictionary significance are obvious:

*Tree*

Habit: Vigorous; upright-spreading.
Fruit production: Good; regular bearer.
Current Growth:

*Surface texture.*—Smooth at first, with lenticels small and minute; with age, becomes larger and cracked, with slightly raised lenticels appearing toward the base of the more vigorous shoots.

*Color.*—At first green or reddish on exposed surfaces, with lenticels appearing as small, nearly white dots.

Two-year wood:

*Surface texture.*—Generally smooth, with slightly raised, irregular, longitudinal striations and numerous lenticles.

*Color.*—Brown.

Old Wood:

*Surface texture.*—Generally smooth, with moderate number of large, raised lenticels, and some small longitudinal fissures.

*Color.*—From grey to greyish brown or reddish brown on more exposed surfaces.

Leaves:

*Size.* — Length — from 5 inches to 6½ inches. Width—from 1¼ inches to 1¾ inches.

*Shape.*—Lanceolate, with apex acuminate.

*Color.*—Dark green on upper surface, with lower surface lighter in color.

*Petiole.*—Medium length.

*Margin.*—From finely serrate to somewhat crenate, and glandular.

*Glands.*—Reniform; medium size; usually from 3 to 5 in number; borne both on the petiole and on the base of the blade.

Vegetative buds:

*Size.*—Small.

*Shape.*—Ovoid, unless compressed between flower buds.

*Scales.*—Pubescence thick and of moderate length.

*Color.*—Dark brown.

*Flowers*

Dates of first and full bloom: Over prolonged period of observation, varied widely from February 8 to March 14 for first bloom, and from February 17 to March 25 for full bloom, due to weather variations from year-to-year.

Dormant flower buds:

*Shape.*—Ovoid.

*Scales.*—Pubescent.

*Color.*—Dark brown.

Size (when fully open): Showy; medium size.

Petalage: Single; usually 5 petals.

Color (open flower): Near Rhodamine Pink, Plate 527/3, page 138 (Wilson), blending with near Phlox Pink, Plate 625/2, page 77 (Wilson) toward base of petal, with small area at attachment near Phlox Pink, Plate 625, page 77 (Wilson).

*Fruit*

Ripening dates: Generally ripens from early to mid-June at Ontario, California; over prolonged period of observation, the dates of first ripening ranged from May 30 to June 23; length of fruit maturation period from peak bloom to first ripe averages from about five days to about a week longer than that for the variety "Robin."

Maturity when described: Eating ripe.

Size: Somewhat variable, but generally medium size.

*Axial diameter.*—From 2⅛ inches to 2½ inches.

*Transverse diameter in suture plane.*—From 2⅜ inches to 2⅝ inches.

*Transverse diameter at right angles to suture plane.*—From 2¼ inches to 2½ inches.

Form: Somewhat variable; slightly unsymmetrical; nearly round; sometimes slightly compressed.

Suture: Usually an inconspicuous line extending from base to apex.

Ventral surface: Rounded; lips slightly unequal.

Stem cavity: Flaring and rounded; elongated somewhat in suture plane, with suture showing on both sides.

*Depth.*—From about ⅜ inch to about ½ inch.

*Width.*—From about 1 inch to about 1¼ inches.

*Markings.*—Distinct red streaks of varying width and length radiate from stem attachment and opposite to suture, often extending nearly to apex, with occasional depression caused by stem.

Base: From rounded to truncate.

Apex: Generally depressed; pistil point slightly oblique.

Stem: Medium caliper; glabrous; medium adherence to stone. Length—about ½ inch.

Skin:

*Thickness.*—Thick.

*Texture.*—Medium.

*Tenacity to flesh.*—From semi-free to free.

*Pubescence.*—Moderate; medium length.

*Color.*—Ground color near Colonial Buff, Plate XXX (Ridgway), usually blending into between Deep Sea-Foam Green, Plate XXXI (Ridgway) and Glass Green, Plate XXXI (Ridgway) at stem end, all heavily overlaid with flecks, streaks, mottling, and blushes from Rose Opal, Plate 022/3, page 110 (Wilson), to Rose Opal, Plate 022, page 110 (Wilson) darkening to near Blood Red, Plate 820, page 166 (Wilson) when becoming overripe.

Flesh:

*Quality.*—Medium firm; melting; fine, tender fibres.

*Aroma.*—Not pronounced.

*Flavor.*—Subacid.

*Color.*—Between white and Naples Yellow, Plate 403/3, page 121 (Wilson), becoming toward the skin near Geranium Lake, Plate 20/3, page 20 (Wilson), flecked with Blood Red, Plate 820/3, page 166 (Wilson), with surface of pit cavity tinged with near Pod Green, Plate 061/3, page 120 (Wilson).

Stone:

*Tenacity of flesh.*—Free, but sometimes adhering somewhat to stone along ventral edge.

*Size.*—From medium to small. Length—from ⅞ inch to 1 inch. Width—from ¾ inch to ⅞ inch. Thickness—from ⅝ inch to ¾ inch.

*Form.*—From globose to obovate.

*Base.*—Somewhat oblique.

*Hilum.*—Narrow; oval.

*Apex.*—From rounded to sometimes acuminate.

*Sides.*—Slightly unequal; irregularly furrowed and pitted throughout.

*Ventral edge.*—Medium thickness; with wing generally throughout.

*Dorsal edge.*—Narrow, with deep groove throughout; ridges on either side generally continuous, with only an occasional interruption.

*Color.*—From near Yellow Ochre, Plate 07/2, page 101 (Wilson) to near Yellow Ochre, Plate 07/3, page 101 (Wilson).

I claim:

A new and distinct variety of peach tree of the white-fleshed, freestone, fruit-bearing type, substantially as herein shown and described, characterized particularly as to novelty by the unique combination of a vigorous habit of tree growth, a chilling requirement about equal to that of the variety "Springtime" (Plant Patent No. 1,268), medium-sized white-fleshed fruit of good subacid flavor, said fruit being almost round in shape, with the apex somewhat depressed and having a very attractive red skin coloring, and a ripening period ranging from about a few days earlier to a few days later than that of the variety "Robin" (Plant Patent No. 529), with a maturation period from peak bloom to first fruit ripening averaging from about five days to a week longer than that of the "Robin" variety aforesaid.

No references cited.